US00PP13170P2

(12) United States Plant Patent
Olesen et al.

(10) Patent No.: US PP13,170 P2
(45) Date of Patent: Nov. 5, 2002

(54) MINIATURE ROSE VARIETY 'POULRA007'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/780,135

(22) Filed: Feb. 8, 2001

(65) Prior Publication Data

US 2001/0025381 P1 Sep. 27, 2001

(51) Int. Cl.[7] ..... A01H 5/00
(52) U.S. Cl. ..... Plt./122
(58) Field of Search ..... Plt./122

(56) References Cited

PUBLICATIONS

UPOV–ROM GTITM Computer Database, 2001/04, GTI Jouve Retrieval Software, citation for 'POUL007'*

* cited by examiner

*Primary Examiner*—Bruce R. Campell
*Assistant Examiner*—Susan B. McCormick

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

BOTANICAL CLASSIFICATION

*Rosa hybrida.*

VARIETY DENOMINATION

'POULra007'.

SUMMARY OF THE INVENTION

The present invention constitutes a new and distinct variety of miniature rose plant which originated from a controlled crossing between 'POULra', described and illustrated in U.S. Plant Pat. No. 11,543 issued Oct. 3, 2000 and 'POULisab', described and illustrated in U.S. Plant patent application Ser. No. 09/270,177 dated Mar. 15, 1999. The two parents were crossed in July 1997 and the resulting seeds were planted in a controlled environment. The new variety is named 'POULra007'.

The new rose may be distinguished from its seed parent, 'POULrac', by the following combination of characteristics:

1. The growth habit of 'POULrac' is smaller.
2. The size of the open bloom of 'POULrac' is smaller than 'POULra007'.
3. The seed parent has more flowers per stem.

The new variety may be distinguished from its pollen parent, 'POULisab' created by the same inventors, by the following combination of characteristics:

1. 'POULisab' is a hybrid tea and much larger in habit.
2. The foliage of the pollen parent is much larger when compared to 'POULra007'.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

This combination of qualities is not present in previously available commercial cultivars of this type and distinguish 'POULra007' from all other varieties of which we are aware.

As part of their rose development program, L. Pernille Olesen and Mogens N. Olesen germinated the seeds from the aforementioned hybridization in winter 1997 and conducted evaluations on the resulting seedlings in a controlled environment in Fredensborg, Denmark.

'POULra007' was selected by the inventors as a single plant from the progeny of the hybridization in spring 1998.

Asexual reproduction of 'POULra007' by cuttings and traditional budding was first done by L. Pernille and Mogens N. Olesen in their nursery in Fredensborg, Denmark in June 1998. This initial and other subsequent propagations conducted in controlled environments have demonstrated that the characteristics of 'POULra007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra007'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULra007', as observed in its growth in Burlington, Ontario, Canada on plants aged sixteen weeks. Root development for the observed plant typically takes 8 to 10 weeks. Color references are made using The Royal Horticultural Society (London, England) Colour Chart, 1995, except where common terms of color are used.

For a comparison, several physical characteristics of the rose variety 'POULrac', a rose variety from the same inventors described and illustrated in U.S. Plant Pat. No. 11,543 and issued on Oct. 3, 2000 are compared to 'POULra007' in Chart 1.

CHART 1

| | 'POULra007' | 'POULrac' |
|---|---|---|
| Bud color at ¼ open | Red-Purple Group 59A | Red Group 53A to Red-Purple Group 60B |
| Upper petal surface, open bloom | Red Group 45B | Between Red Group 46A and Red-Purple Group 60B |
| Size of pot plant | 20–22 cm (h) × 18–20 cm (w) | 16–18 (h) × 16–18 (w) |

Classification:
(*Genus, species, cultivar*).—*Rosa Hybrida* POULra007.
*Commercial.*—Miniature.
Parents: 'POULrac'×'POULisab'.

FLOWER AND FLOWER BUD

Blooming habit: Continuous.
Flower bud:
*Size.*—Upon opening, 25–28 mm in length from base of receptacle to end of bud.
*Bud form.*—Short and pointed ovoid.
*Bud color.*—As sepals unfold, Red-Purple Group 59A. Red-Purple Group 59A at ¼ opening.
*Sepals.*—Green Group 143A. Weak foliaceous appendages on 3 of the 5 sepals. Surfaces of sepals strongly pubescent. Stipitate glands are generally absent from sepals. Sepals are 10 to 12 mm long and 8 mm wide.
*Receptacle.*—Surface: Smooth. Shape: Urn-shaped. Size: Small. 8–10 mm(h)×8–10 mm (w). Color: Yellow-Green Group 144B.
*Peduncle.*—Surface: Small stipitate glands present. Length: 30–40 mm average length. Color: Yellow-Green Group 144B. Strength: Erect. Anthocyanin: None.
*Borne.*—Multiple buds per flowering stem.
Flower bloom:
*Fragrance.*—None.
*Duration.*—As a pot plant, flowers last from 14 to 18 days. As a cut flower 12 to 14 days. The blooms have a duration on the plant of approximately 16 to 18 days.
*Size.*—Large for a 8–11 cm pot rose. Average flower diameter is 50 mm when open.
*Form.*—Shape of flower when viewed from the side: Upon opening, upper part: Flattened convex. Upon opening, lower part: Flattened convex. Open flower, upper part: Convex. Open flower, lower part: Convex.
*Petalage*—Very double. Average range: 40–50 petals under normal conditions with 0–5 petaloids.
Color:
*Upon opening, petals.*—Outermost petals: Outer Side: Red-Purple Group 61A–B. Inner Side: Red Group 53B. Innermost petals: Outer Side: Red-Purple Group 60B. Inner Side: Red Group 53B. Some inner petals exhibit stripes of Red Group 36D from basal zone to center of middle zone of petals.
*Upon opening, basal petal spots.*—Outermost petals: Outer Side: Yellow-Green Group 145A. Inner Side: Yellow-Green Group 154C. Innermost petals: Outer Side: White Group 155C. Inner Side: White Group 155B.
*After opening, petals.*—Outermost petals: Outer Side: Red Group 53A–B. Inner Side: Red Group 45B. Innermost petals: Outer Side: Red Group 53C. Inner Side: Red Group 53B–C. Innermost petals exhibit occasional stripe of White Group 155A emanating from basal zone to center of marginal zone.
*After opening, basal petal spots.*—Outermost petals: Outer Side: Green-White Group 157A. Inner Side: Yellow-White Group 158B. Innermost petals: Outer Side: Yellow Group 3C. Inner Side: Yellow Group 3B.
General tonality: On open flower, Red Group 45B. No change in the general tonality at the end of the 14$^{th}$ day. Afterwards, general tonality is Red-Purple Group 60A–B.
Petals:
*Petal reflex.*—Strongly.
*Petal edge.*—Entire.
*Shape.*—Deltoid; base is flat at union with receptacle.
*Petaloids.*—Present. Quantity: 0–5.
*Thickness.*—Thick.
*Arrangement.*—Imbricated.
*Size.*—Petals are 15 mm long and 10–12 mm wide.
Reproductive organs:
*Pollen.*—Color: Yellow-Orange Group 20A. Quantity: Very abundant.
*Anthers.*—Size: Small. Color: Greyed-Yellow Group 160D. Quantity: Average.
*Filaments.*—Color: Yellow-Orange Group 17C with intonations of Orange-Red Group 33B.
*Stigmas.*—Very slightly superior in location to anthers. Color: Red Group 53D with tips of stigmas Red Group 56C–D.
*Styles.*—Color: Red Group 53C.
*Hip formation.*—Not observed.

PLANT

Plant growth: Vigorous and compact. When grown as an 8–11 cm pot plant, the average height of the plant itself is 20–22 cm and the average width is 18–20 cm.
Stems:
*Color.*—Young wood: Green Group 143B. Older wood: Green Group 143A.
*Prickles.*—Incidence: Moderate. Size: Average length: 2–3 mm. Color: Greyed-Yellow Group 160D. Shape: Concave.
*Surface.*—Young wood: Smooth. Older wood: Smooth.
*Length.*—Stem length is typically 20 to 25 cm.
*Diameter.*—Stem diameter is typically 4 to 6 mm.
Plant foliage: Typcial number of leaflets on normal leaves in middle of the stem: 5 leaflets.
*Typical leaf size.*—Small. 60–70 mm (l)×45–50 mm (w).

*Quantity.*—Somewhat profuse.

*Color.*—Mature foliage: Upper leaf surface: Green Group 139A. Lower leaf surface: Green Group 137C. Juvenile foliage: Upper leaf surface: Green Group 137B. Lower leaf surface: Green Group 135B. Anthocyanin: On lower leaf surface of juvenile foliage. Color: Intonations of Greyed-Orange Group 172D to Greyed-Red Group 181B.

Plant leaves and leaflets:

*Stipules.*—Size: 5 mm (l)×3 mm (w). Color: Green Group 143C. Presence of stipitate glands: Located along margins of stipules. Anthocyanin: None.

*Petiole.*—Length: 12–15 mm. Color: Green Group 143B. Underneath: Generally smooth. Margins: Stipitate glands. Anthocyanin: Along upper margins of mature and juvenile petiole. Color: Greyed-Purple Group 183A.

*Rachis.*—Color: Green Group 143C. Underneath: Occasional small prickles. Margins: Smooth. Anthocyanin: Along upper surface margins of mature and juvenile rachis. Color: Greyed-Purple Group 183A.

*Leaflet.*—Edge: Finely serrated. Shape: Pointed ovate. Other: Modeately glossy and thick.

Disease resistance: Above average resistance to mildew, black spot, and Botrytis under normal growing conditions in Burlington, Canada.

Cold hardiness: 'POULra007' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant, red flowers, vigorour growth, compact habit, suitability for production from softwood cuttings in pots, and durable flowers and foliage which make the variety suitable for distribution in the floral industry.

* * * * *

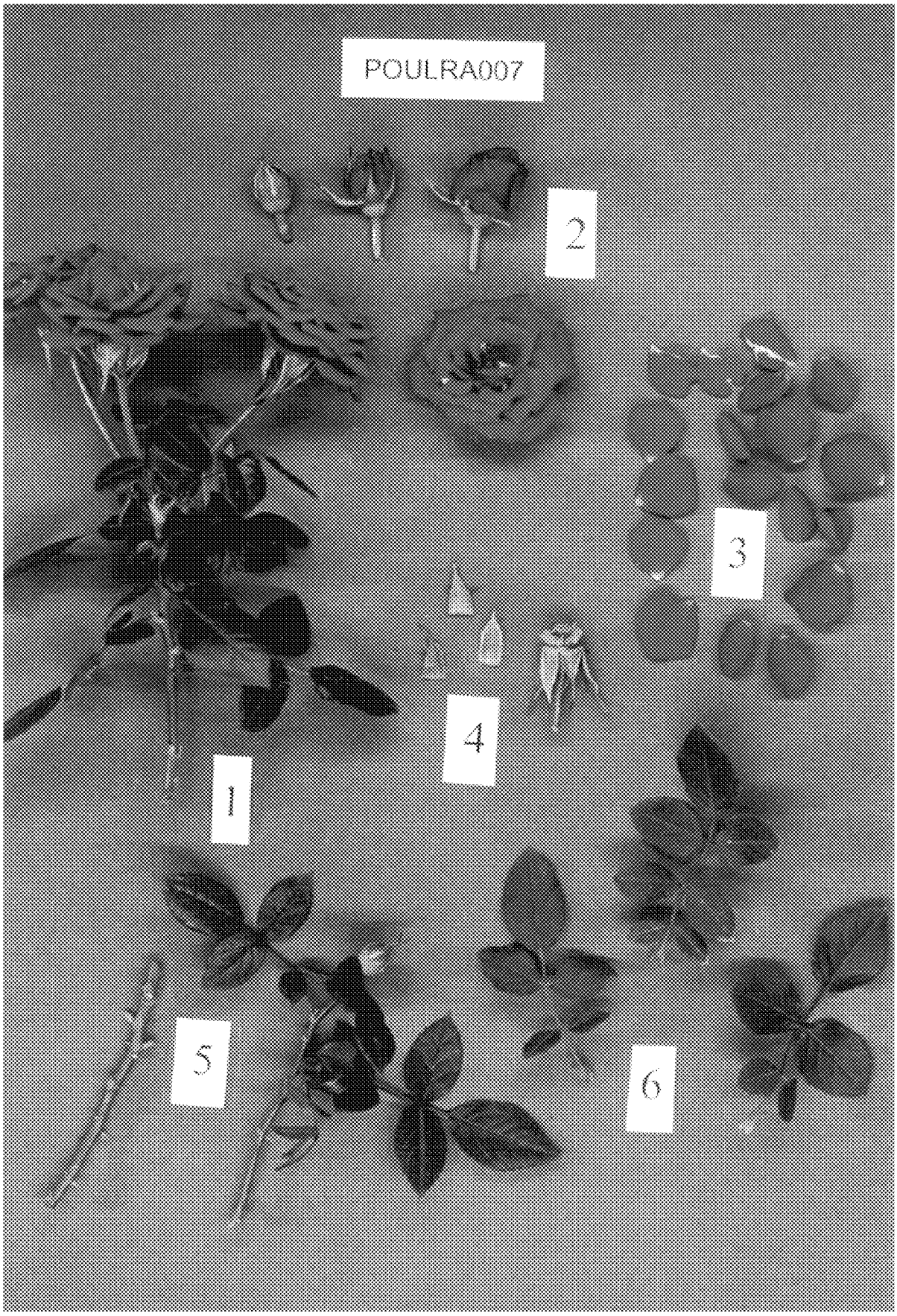
POULRA007
1
2
3
4
5
6